United States Patent
Xu et al.

(10) Patent No.: US 10,392,351 B2
(45) Date of Patent: Aug. 27, 2019

(54) METHOD FOR PREPARING NILOTINIB INTERMEDIATE

(71) Applicants: SUZHOU LIXIN PHARMACEUTICAL CO., LTD, Suzhou (CN); Xuenong Xu, Suzhou (CN)

(72) Inventors: Xuenong Xu, Suzhou (CN); Deli Zeng, Suzhou (CN); Liang Shu, Suzhou (CN); Qing Zhang, Suzhou (CN); Zhijian Bao, Suzhou (CN); Jia Xue, Suzhou (CN); Jian Su, Suzhou (CN); Zhe Wang, Suzhou (CN); Wenjie Zhou, Suzhou (CN); Lingling Xie, Suzhou (CN)

(73) Assignees: SUZHOU LIXIN PHARMACEUTICAL CO., LTD., Suzhou (CN); Xuenong Xu, Suzhou (CN)

( * ) Notice: Subject to any disclaimer, the term of this patent is extended or adjusted under 35 U.S.C. 154(b) by 0 days.

(21) Appl. No.: 15/203,904

(22) Filed: Jul. 7, 2016

(65) Prior Publication Data
US 2016/0311777 A1    Oct. 27, 2016

Related U.S. Application Data

(63) Continuation of application No. PCT/CN2014/094891, filed on Dec. 25, 2014.

(30) Foreign Application Priority Data

Jan. 7, 2014    (CN) .......................... 2014 1 0005290

(51) Int. Cl.
C07D 233/61    (2006.01)
(52) U.S. Cl.
CPC ................. C07D 233/61 (2013.01)
(58) Field of Classification Search
CPC .................................................. C07D 233/61
USPC ....................................................... 548/343.5
See application file for complete search history.

(56) References Cited

FOREIGN PATENT DOCUMENTS

| | | |
|---|---|---|
| CN | 101189212 A | 5/2008 |
| CN | 103694176 A | 4/2014 |
| EP | 2305667 A2 | 4/2011 |
| WO | 2004/000528 A2 | 12/2003 |
| WO | 2006/022026 A1 | 3/2006 |
| WO | 2006/135640 A2 | 12/2006 |
| WO | 2006/135641 A2 | 12/2006 |
| WO | WO-2006135640 A2 * | 12/2006 ........... C07C 205/12 |
| WO | 2008/038042 A1 | 4/2008 |
| WO | 2009/049028 A1 | 4/2009 |
| WO | 2010/009402 A2 | 1/2010 |

OTHER PUBLICATIONS

Huang, Wei-Sheng and William Shakespeare, "An Efficient Synthesis of Nilotinib (AMN107)", Synthesis (2007), 14: pp. 2121-2124. (Year: 2007).*

* cited by examiner

*Primary Examiner* — Matthew P Coughlin
*Assistant Examiner* — Sagar Patel
(74) *Attorney, Agent, or Firm* — Schwegman, Lundberg & Woessner P.A.

(57) ABSTRACT

Disclosed in the present invention is a method for preparing nilotinib intermediate 3-(4-methyl-1H-imidazol-1-yl)-5trifluoromethyl phenylamine (I). The method comprises the following steps: taking trifluorotoluene as an initial material, and preparing the nilotinib intermediate (I) by nitration, bromization, condensation and reduction successively Compared with the prior art, the preparation method has the following advantages: a relatively high yield, the raw materials are easily obtained, a concise process and few side reactions, and is adapted to industrial production, so the development of an economic technology of the bulk drug is promoted.

4 Claims, No Drawings

METHOD FOR PREPARING NILOTINIB INTERMEDIATE

CROSS REFERENCE TO RELATED APPLICATIONS

This application is a continuation of PCT/CN2014/094891 filed Dec. 25, 2014, which claims priority to CN 201410005290.9 filed Jan. 7, 2014, both of which are incorporated herein by reference.

TECHNICAL FIELD

This invention relates to the technical field of organic synthesis route design and preparation of API and intermediates, in particular, to the method for preparing nilotinib intermediate.

BACKGROUND ART

Nilotinib (Nilotinib, chemical name: 4-Methyl-3-[4-(3-pyridinyl)-2-pyrimidinyl)amino)-N-[5-(4-methyl-1H-imidazol-1-yl)-3-(trifluorom ethyl)phenyl]benzamide) is a high-selectivity oral tyrosine kinase inhibitor developed by Novartis. Its monohydrochloride monohydrate was approved for marketing by US FDA in October 2007, with its trade name as Tasigna. Clinically, it is used for the treatment of chronic myelocytic leukemia (CML) which is ineffective by use of imatinib mesylate. The drug can, through targeting effect, selectively inhibit tyrosinase and philadelphia chromosome positive CIVIL caused by encoding gene mutation, with a good patient tolerance, strong selectivity, and a significant curative effect.

There have been a lot of reports about the preparation method of Nilotinib, most of which relates to two important intermediates: 3-(4-methyl-1H-imidazol-1-yl)-5-trifluorom ethyl phenylamine (I) and 4-Methyl-3-[[4-(3-pyridinyl)-2-pyrimidinyl]amino] benzoic acid(II).

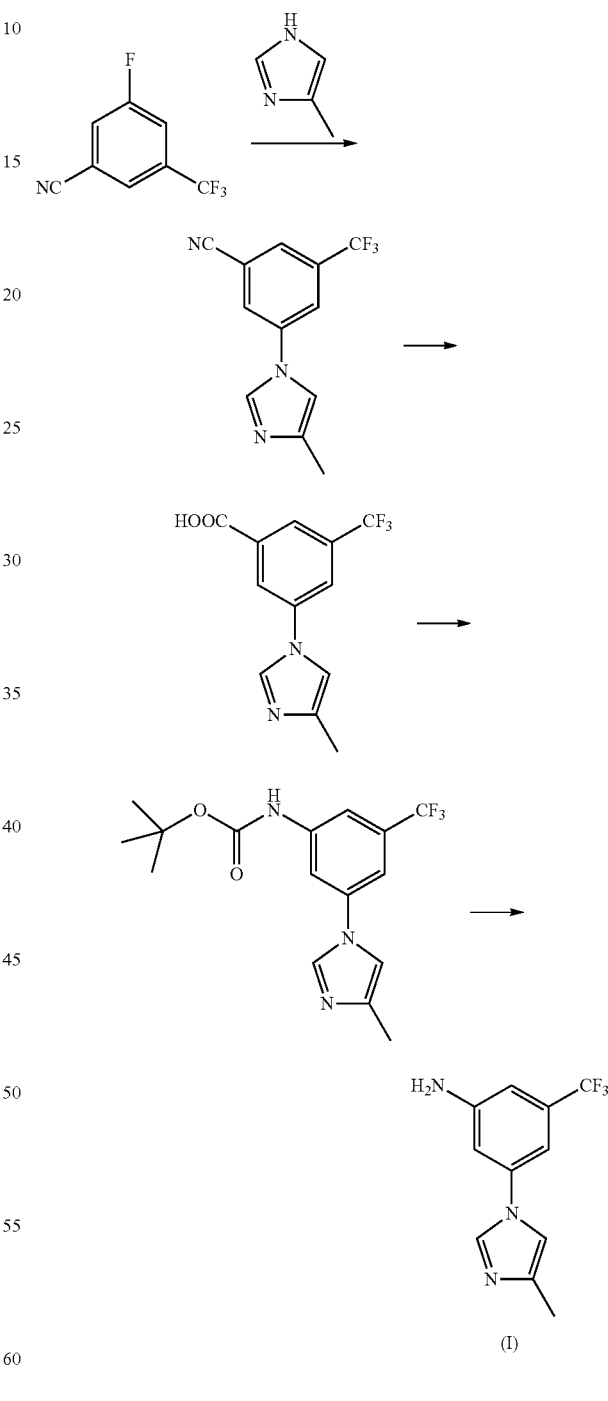

The preparation of intermediate (I) mainly includes the following several synthetic routes:

Patents WO2004/00528 and WO2006/135640 reported the synthesis method of the targeted intermediate (I) through nucleophilic substitution, hydrolysis reaction, Curtius rearrangement reaction and hydrolysis reaction by using 3-fluoro-5-(trifluoromethyl)benzonitrile and 4-methyl-1H-imidazole as raw materials.

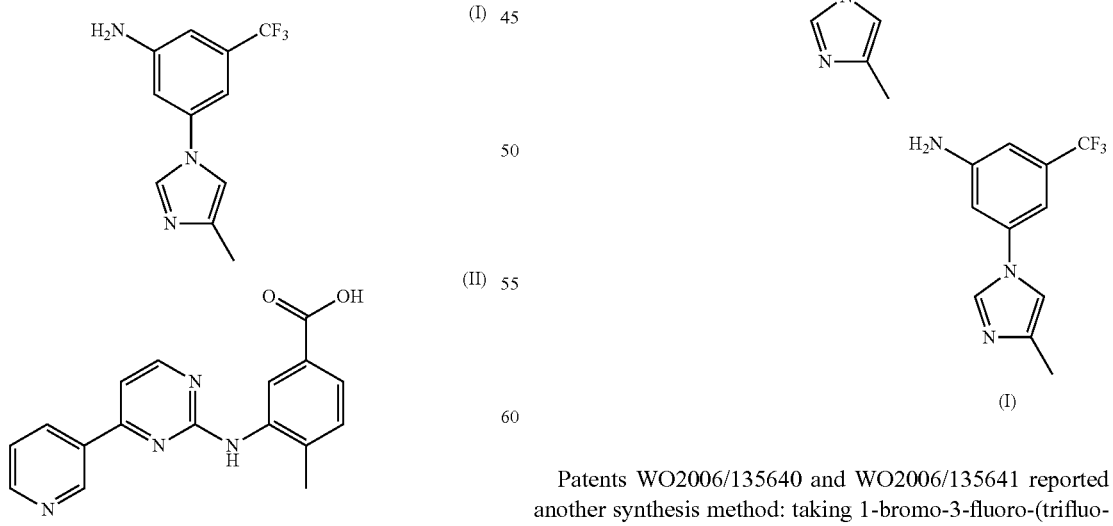

Patents WO2006/135640 and WO2006/135641 reported another synthesis method: taking 1-bromo-3-fluoro-(trifluoromethyl)benzene and 4-methyl-1H-imidazole as raw materials, to get the targeted intermediate (I) through nucleophilic substitution and hydrolysis reaction.

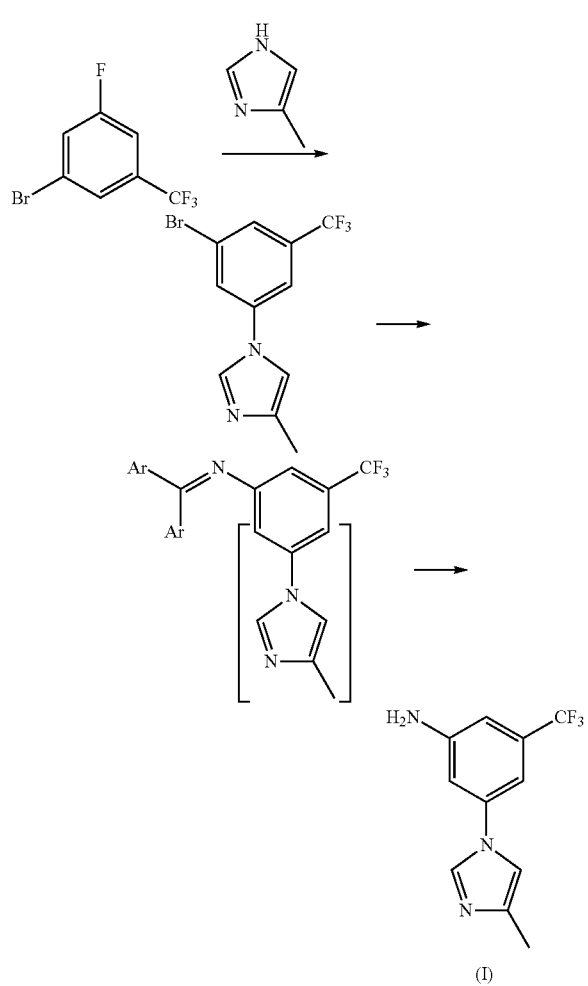

(I)

The above patents also reported a synthesis method of taking 1-bromo-4-fluoro-2-trifluorotoluene as raw material, and preparing the targeted intermediate (I) by nitration, reduction, and nucleophilic substitution successively.

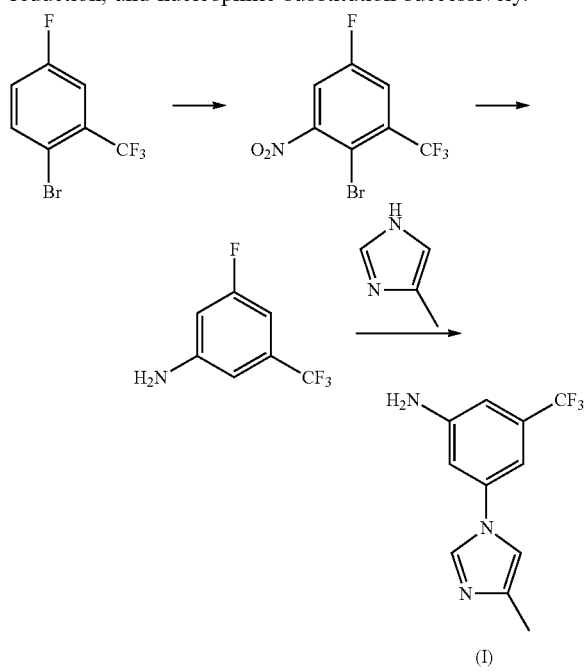

(I)

Patents WO2006/022026, WO2008/038042 and the *Chinese Journal of Pharmaceuticals* (P. 17, Issue 1, Volume 44, 2013) reported a method for preparing the targeted intermediate (I) through double nitration reaction, substitution and reduction by using trifluorotoluene as raw material.

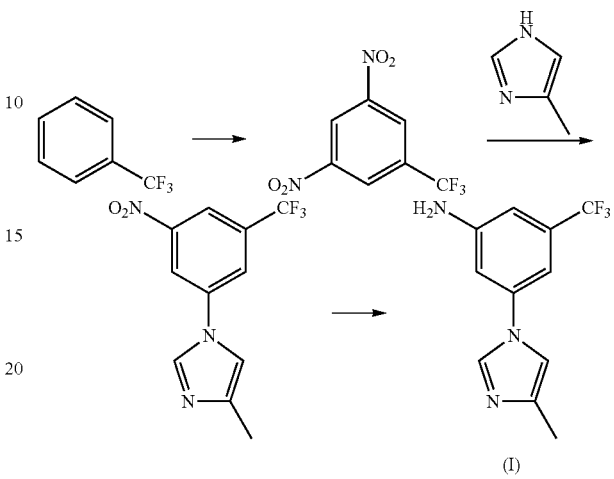

(I)

Patents WO2009/049028, WO2010/009402 and the *Synthesis* (P. 2121, Volume 14, 2007) reported a relatively common preparation method: taking 3-Fluorotoluene as an initial material, and preparing the targeted intermediate (I) by single nitration, bromination, reduction, condensation and substitution reaction.

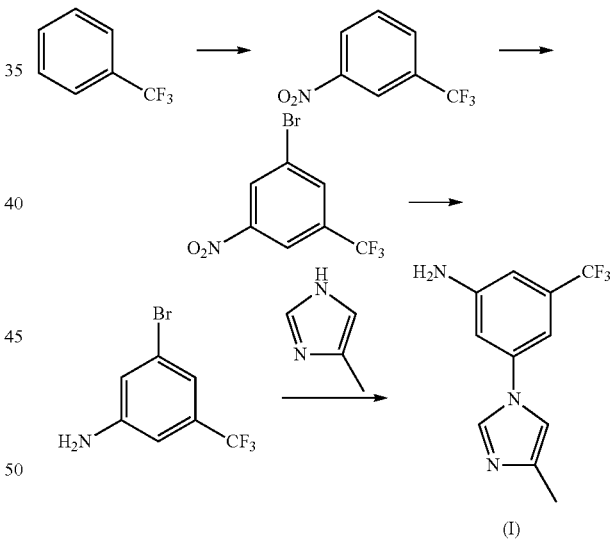

(I)

By investigation of the present preparation methods of nilotinib intermediate (I), many of them have problems such as very rare raw materials, long steps, high cost and low yield, etc. Comparatively speaking, the most common method is to reduce 3-bromo-5-nitro-trifluorotoluene to get corresponding amide 3-bromo-5-trifluoromethyl-aniline, and then get the targeted product through condensation, because the activation and benzene ring after nitro is reduced to amino make it easier to achieve the subsequent condensation reaction based on the mechanism of nucleophilic substitution. This method was reported in literature up to 70%. In the research process, the inventor found that this route has a relatively high yield, but in the actual reaction process, due to different selection of temperature, type and dosage of catalyst, and acid-binding agent, the raw material's own functional group's bromine and amino will have self-coupling condensation in different extent, with over 50% coupled products, thus influencing the effect of industrialized enlargement.

To fundamentally solve the self-coupling problem of 3-bromo-5-trifluoromethyl-aniline, the best choice is to conduct condensation reaction before 3-bromo-5-nitro-trifluorotoluene is reduced, so as to get 3-(4-methyl-1H-imidazol-1-yl)-5-nitro-trifluorotoluene, then conduct reduction reaction of nitro, to get the targeted product, nilotinib intermediate (I). This new design thought overcomes the occurrence of side reaction of coupling, because nitro is unable to have self-coupling condensation reaction with bromine. However, the inactivation of nitro greatly reduces the activity of the targeted condensation reaction. Patent WO2006/135640 reported this synthetic route: under the action of catalyst and alkali, 3-bromo-5-nitro-trifluorotoluene and 4-methyl-1H-imidazole have condensation reaction, with a yield of only 20-25%, thus it further loses the value of industrial production.

Therefore, it is necessary to find a new preparation method of nilotinib intermediate 3-(4-methyl-1H-imidazol-1-yl)-5-trifluoromethyl phenylamine (I), of which the raw materials are easily obtained, and it is easy to operate with few side reactions and environmental pollution.

SUMMARY OF THE INVENTION

The object of the invention is to provide an improved method for preparing nilotinib intermediate 3-(4-methyl-1H-imidazol-1-yl)-5-trifluorom ethyl phenyl amine (I). Through selection and optimization of promoter, mixed acid-binding agent and proper temperature in the condensation reaction, and through richer reduction method, it can greatly improve the yield of the targeted product, and its raw materials are easily obtained, it has few side reactions and it is suitable for industrial production.

To achieve the above object, the present invention adopts the following main technical solutions: a method for preparing nilotinib intermediate 3-(4-methyl-1H-imidazol-1-yl)-5-trifluoromethyl phenylamine (I).

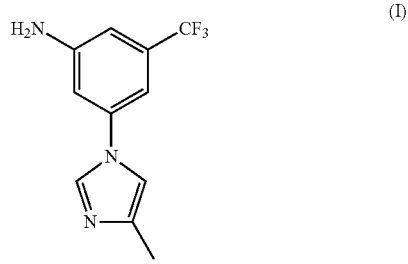 [SMILES: Cc1cn(-c2cc(N)cc(C(F)(F)F)c2)cn1]

Wherein the preparation method comprises the following steps: taking trifluorotoluene as an initial material, to get nitrobenzotrifluoride through nitration reaction, by bromination reaction, to get 3-bromo-5-nitro-trifluorotoluene, and then 3-bromo-5-nitro-trifluorotoluene and 4-methyl-1H-imidazole have condensation reaction to produce 3-(4-methyl-1H-imidazol-1-yl)-5-nitro-trifluorotoluene under the action of catalyst, promoter and mixed acid-binding agent, and through reduction reaction, to produce nilotinib intermediate (I).

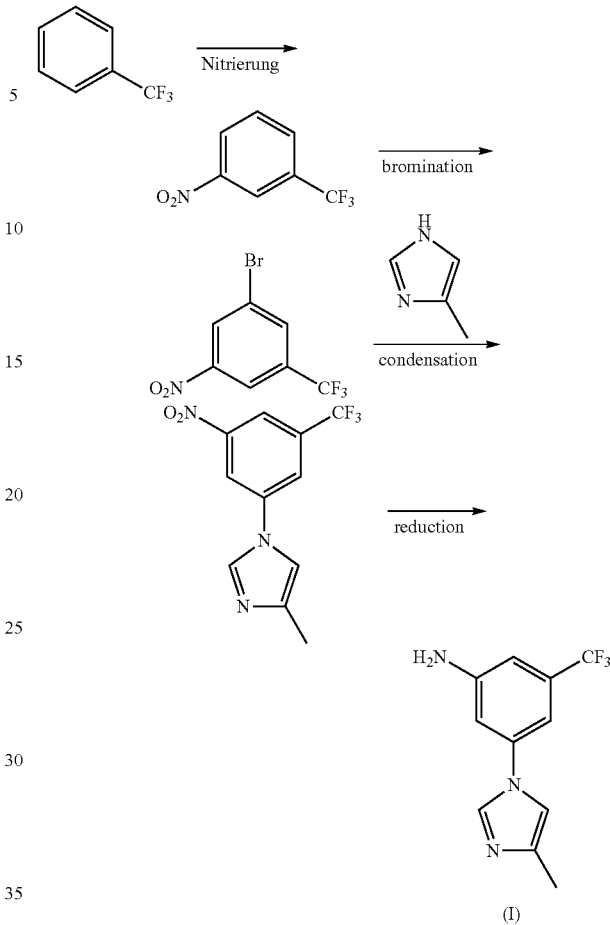

In addition, the invention further provides the following additional technical solutions:

The catalyst for the condensation reaction is cuprous iodide, zinc iodide, stannous chloride, palladium chloride or silver iodide, preferably cuprous iodide.

The promoter for the condensation reaction is 8-hydroxyquinoline, 2,6-dimethylpyridine, 4-dimethylaminopyridine, N-methylmorpholine, N-ethyl morpholine, 1,5-diazabicyclo [4.3.0]-non-5-ene, 1,8-diazabicyclo [5.4.0]-undec-7-ene or 1,4-diazabicyclo[2.2.2] octane, preferably 8-hydroxyquinoline or 1,8-diazabicyclo [5.4.0]-undec-7-ene.

The mixed acid-binding agent for the condensation reaction consists of any of sodium hydride, potassium hydride, sodium hydroxide, potassium hydroxide, sodium carbonate, potassium carbonate, sodium tert-butoxide, potassium tert-butoxide, sodium methylate or sodium ethoxide and any one of triethylamine, ethanediamine or diisopropylethylamine, preferably potassium carbonate and triethylamine or potassium tert-butoxide and ethanediamine.

The solvent for the condensation reaction is dimethylbenzene, dioxane, dimethylsulfoxide, N,N-dimethylformamide or N,N-dimethylacetamide, preferably dimethylsulfoxide or N,N-dimethylformamide.

The temperature for the condensation reaction is 120-160° C., preferably 130-150° C.

The reducing agent for the reduction reaction is iron, zinc, stannum, sodium hydrosulfite, hydrazine hydrate or hydrogen, preferably hydrazine hydrate or hydrogen.

When the reducing agent is hydrogen, the catalyst for the hydrogenation reaction is palladium-carbon, raney nickel, palladium hydroxide or platinum carbon, preferably palladium-carbon.

Compared to the prior art, the preparation method in the present invention has the following advantages: through selection and optimization of catalyst, promoter, mixed acid-binding agent and proper temperature in condensation reaction, it improves the activity of condensation reaction, overcomes the inactivation of nitro on aryl, improves the conversion rate of the condensation reaction, and further improves the atom economy, selectivity of reaction and controllability of operation, thus making the production of nilotinib intermediate (I) more controllable, greatly reducing the cost, and facilitating the economic and technological development of the API.

DETAILED DESCRIPTIONS OF THE PREFERRED EMBODIMENTS

The invention is further described in details in combination with several preferred embodiments.

Embodiment I 15 mL of concentrated nitric acid (60-65%) and 30 mL of concentrated sulfuric acid (98%) were mixed into mixed acid at 0-10° C., added dropwise 29.2 g of trifluorotoluene (29.2 g, 0.2 mol) at 0-5° C., reacted for 8 hours at room temperature, to complete the reaction detected by TLC. Poured the reaction solution into ice water, extracted with ethyl acetate, washed with 10% sodium hydroxide, and dried, the solvent was removed under a reduced pressure condition, to get 34.0 g of light yellow transparent liquid nitrobenzotrifluoride, with a yield of 89.0%, boiling point 105-107° C. (4 kPa), and the next reaction can be started with no need for purification.

Embodiment II

Under 100 mL concentrated sulfuric acid ice-water bath, added 19.1 g (0.1 mol) of nitrobenzotrifluoride, added dropwise liquid bromine (15.8 g, 0.1 mol) by batch at room temperature, controlled the reaction temperature at 60-70° C. to react for 14 hours, to complete the reaction detected by TLC. Leaved it standstill for layering, washed the organic phases with 5% sodium hydroxide and saturated salt water, concentrated, to get 24.7 g of orange red oily matter 3-bromo-5-nitro-trifluorotoluene, with a yield of 91.8%, boiling point 74-76° C. (70 Pa); EI-MS (m/z): 269 (M+H); 1H NMR (400 MHz, CDCl$_3$) δ 8.59-8.60 (m, 1H), 8.46 (m, 1H), 8.12 (m, 1H).

Embodiment III 13.5 g of 3-bromo-5-nitro-trifluorotoluene (13.5 g, 0.05 mol), 5.0 g of 4-methyl-1H-imidazole (5.0 g, 0.06 mol), 1.42 g of cuprous iodide (1.42 g, 7.5 mmol), 2.2 g of 8-hydroxyisoquinoline (2.2 g, 7.5 mmol), 7.6 g of potassium carbonate (0.055 mol) and 50 mL of N,N-dimethylformamide were added to a 250 mL three-necked bottle, heated to 100° C., stirred to dissolve. Added with 0.75 g of triethylamine (0.75 g, 7.5 mmol), continued to heat to 140° C., reacted for 5 hours, to complete the reaction detected by TLC. Cooled down to 50-60° C., filtered, and the filter cake was washed with ethyl acetate, the filter liquor was washed with saline water and water, concentrated, then recrystallized by ethyl acetate and n-hexane (1:1), to get 10.6 g of yellow solid 3-(4-methyl-1H-imidazol-1-yl)-5-nitro-trifluorotoluene, with a yield of 78.2%, melting point 118-120° C., MS-ESI (m/z): 272 (M+H), 1H NMR (400 MHz, CDCl$_3$) δ 8.45 (s, 2H), 7.95 (s, 1H), 7.93 (s, 1H), 7.16 (s, 1H), 2.33 (s, 3H).

Embodiment IV 2.71 g of 3-(4-methyl-1H-imidazol-1-yl)-5-nitro-trifluorotoluene (2.71 g, 10 mmol), 0.27 g of ferric trichloride (0.27 g, 1 mmol), 0.4 g of activated carbon and 50 mL of ethyl alcohol were added, at room temperature, added dropwise 80% hydrazine hydrate (1.25 g, 20 mmol), heated to 50-60° C., reacted for 4-5 hours, filtered, concentrated to remove ethyl alcohol, and the resulting residue was recrystallized by ethyl alcohol to get 2.2 g of off-white solid nilotinib intermediate 3-(4-methyl-1H-imidazol-1-yl)-5-trifluoromethyl phenylamine (I), with a yield of 91.3%, melting point 127-129° C., MS-ESI (m/z): 242 (M+H), 1H NMR (400 MHz, CDCl$_3$) δ 7.75 (s, 2H), 7.01 (s, 1H), 6.95 (s, 1H), 6.84 (s, 1H), 6.79 (s, 1H), 4.10 (brs, 2H), 2.29 (s, 3H).

Embodiment V 2.71 g of 3-(4-methyl-1H-imidazol-1-yl)-5-nitro-trifluorotoluene (2.71 g, 10 mmol), 0.14 g of 10% palladium-carbon (0.14 g, 5% w/w) and 150 mL of ethyl alcohol were added to the hydrogenation reactor, after air change according to the operating procedure of hydrogenation, heated to 50-55° C., controlled the hydrogen pressure at 5-8 Kg/cm$^2$, until no longer absorb hydrogen for about 4 hours; filtered, and recycled the catalyst, concentrated the reaction solution to remove ethyl alcohol, and the resulting residue was recrystallized by ethyl acetate and n-hexane (1:2-4) to get 2.1 g of off-white solid nilotinib intermediate 3-(4-methyl-1H-imidazol-1-yl)-5-trifluoromethyl phenylamine (I), with a yield of 87.1%, melting point 127-129° C., MS-ESI (m/z): 242 (M+H), 1H NMR (400 MHz, CDCl$_3$) δ 7.75 (s, 2H), 7.01 (s, 1H), 6.95 (s, 1H), 6.84 (s, 1H), 6.79 (s, 1H), 4.10 (brs, 2H), 2.29 (s, 3H).

The foregoing invention has been described in detail by way of illustration and example for purposes of clarity and understanding. As is readily apparent to one skilled in the art, the foregoing are only some of the methods and compositions that illustrate the embodiments of the foregoing invention. It will be apparent to those of ordinary skill in the art that variations, changes, modifications and alterations may be applied to the compositions and/or methods described herein without departing from the true spirit, concept and scope of the invention.

The invention claimed is:

1. A method for preparing a nilotinib intermediate 3-(4-methyi-IH-imidazol-1-yl)-5-trifluoromethyl phenylamine (I),

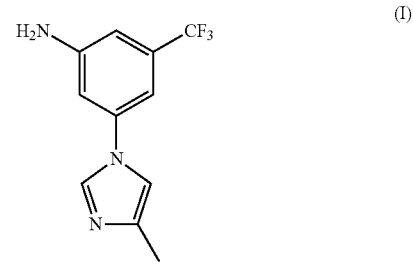

comprising the following steps:
a) converting trifluorotoluene to a nitrobenzotrifluoride through a nitration reaction;
b) converting the nitrobenzotrifluoride to 3-bromo-5-nitro-trifluorotoluene by a bromination reaction;

c) reacting 3-bromo-5-nitro-trifluorotoluene and 4-methyl-1H-imidazole by a condensation reaction to produce 3-(4-methyl-1H-imidazol-1-yl)-5-nitrotrifluorotoluene in the presence of a catalyst, a promoter and a combination of two mixed acid-binding agents at a temperature of 130-160° C., with a yield of the condensation reaction higher than 70%; and d) reducing 3-(4-methyl-1H-imidazol-1-yl)-5-nitrotrifluorotoluene through a reduction reaction to produce the nilotinib intermediate (I);

wherein:

the catalyst for the condensation reaction is cuprous iodide, zinc iodide, stannous chloride, palladium chloride or silver iodide;

the promoter for the condensation reaction is 8-hydroxyquinoline, 2,6-dimethylpyridine, 4-dimethylaminopyridine, N-methylmorpholine, N-ethyl morpholine, 1,5-diazabicyclo[4.3.0]-non-5-ene, 1,8-diazabicyclo[5.4.0]-undec-7-ene or 1,4-diazabicyclo[2.2.2] octane; and the mixed acid-binding agents for the condensation reaction consists of a first mixed acid-binding agent selected from the group consisting of sodium hydride, potassium hydride, sodium hydroxide, potassium hydroxide, sodium carbonate, potassium carbonate, sodium tert-butoxide, potassium tert-butoxide, sodium methylate and sodium ethoxide, and a second mixed acid-binding agent selected from the group consisting of triethylamine, ethanediamine and diisopropylethylamine;

wherein:

there is a mole ratio of 1.1:0.15 between the first mixed acid-binding agent and the second mixed acid-binding agent;

there is a mole ratio of 1:1.2:0.15 between the 3-bromo-5-nitro-trifluorotoluene, 4-methyl-1H-imidazole, and catalyst; and there is a mole ratio of 1:0.15 between the 3-bromo-5-nitro-trifluorotoluene and the promoter.

2. The method for preparing nilotinib intermediate according to claim 1, wherein the condensation reaction comprises carrying out the condensation reaction in a solvent selected from the group consisting of dimethylbenzene, dioxane, dimethylsulfoxide, N,N-dimethylformamide, and N,N-dimethylacetamide.

3. The method for preparing nilotinib intermediate according to claim 1, wherein the reduction reaction comprises carrying out the reduction reaction in the presence of a reducing agent selected from the group consisting of iron, zinc, stannum, sodium hydro sulfite, hydrazine hydrate, and hydrogen.

4. The method for preparing nilotinib intermediate according to claim 3, wherein the reduction reaction in the presence of hydrogen (hydrogenation reaction), comprises carrying out the hydrogenation reaction in the presence of a catalyst selected from the group consisting of palladium-carbon, raney nickel, palladium hydroxide, and platinum carbon when the reducing agent is hydrogen.

* * * * *